(12) United States Patent
Trutwig et al.

(10) Patent No.: US 10,932,351 B2
(45) Date of Patent: Feb. 23, 2021

(54) ELECTRODE ARRAY FOR A DIELECTRICALLY IMPEDED PLASMA TREATMENT

(71) Applicant: Cinogy GmbH, Duderstadt (DE)

(72) Inventors: Leonhard Trutwig, Duderstadt/Gerlingerode (DE); Mirko Hahnl, Berlingerode (DE); Karl-Otto Storck, Duderstadt (DE); Dirk Wandke, Heilbad Heiligenstadt (DE); Matthias Kopp, Gieboldehausen (DE)

(73) Assignee: CINOGY, GMBH, Duderstadt (DE)

( * ) Notice: Subject to any disclaimer, the term of this patent is extended or adjusted under 35 U.S.C. 154(b) by 91 days.

(21) Appl. No.: 15/765,573

(22) PCT Filed: Sep. 26, 2016

(86) PCT No.: PCT/DE2016/100446
§ 371 (c)(1),
(2) Date: Apr. 3, 2018

(87) PCT Pub. No.: WO2017/067535
PCT Pub. Date: Apr. 27, 2017

(65) Prior Publication Data
US 2018/0295708 A1    Oct. 11, 2018

(30) Foreign Application Priority Data

Oct. 19, 2015 (DE) ............ 10 2015 117 715.3

(51) Int. Cl.
*H01J 37/32* (2006.01)
*H05H 1/24* (2006.01)
(Continued)

(52) U.S. Cl.
CPC .......... *H05H 1/2406* (2013.01); *A61L 2/0011* (2013.01); *A61L 2/14* (2013.01);
(Continued)

(58) Field of Classification Search
CPC ......... H05H 1/2406; H05H 2001/2418; H05H 2001/2412; H05H 2245/122; A61L 2/0011; A61L 2/14; A61N 1/04
See application file for complete search history.

(56) References Cited

U.S. PATENT DOCUMENTS

2006/0042545 A1    3/2006   Shibata et al.
2012/0259270 A1   10/2012   Wandke et al.
(Continued)

FOREIGN PATENT DOCUMENTS

CH     102036460 A    4/2011
CN       1522102 A    8/2004
(Continued)

*Primary Examiner* — Yuechuan Yu
(74) *Attorney, Agent, or Firm* — W&C IP (57) ABSTRACT

The invention relates to an electrode array for a dielectrically impeded plasma treatment of a surface of an electrically conductive body used as a counter electrode, comprising a flexible planar electrode (1) and a dielectric (2) of a planar flexible material, which by way of a layer (3) preventing a direct current flow shields the electrode (1) from the surface to be treated. By way of a structure having projections, the dielectric (2) can rest upon the surface to be treated, wherein air spaces for forming the plasma are formed in between the projections. The producibility in particular is improved in that the structure is a lattice structure (6) of adjoining walls (7, 8) that limit a plurality of chambers (9) forming the air spaces, and in that the chambers (9) have a bottom-side closure through the layer (3) of the dielectric (2) preventing the direct current flow and have a face that is open to the surface to be treated, the contact surface of which face consists of end edges (10) of the walls (7, 8) of the lattice structure (6) on the surface to be treated.

13 Claims, 10 Drawing Sheets (51) Int. Cl.
 *A61L 2/14* (2006.01)
 *A61L 2/00* (2006.01)
 *A61N 1/04* (2006.01)

(52) U.S. Cl.
 CPC ....... *A61N 1/04* (2013.01); *H05H 2001/2412* (2013.01); *H05H 2001/2418* (2013.01); *H05H 2245/122* (2013.01)

(56) References Cited

U.S. PATENT DOCUMENTS

| | | |
|---|---|---|
| 2013/0345620 A1 | 12/2013 | Zemel et al. |
| 2014/0182879 A1 | 8/2014 | Busse et al. |
| 2015/0216026 A1 | 7/2015 | Wandke et al. |
| 2016/0236002 A1 | 8/2016 | Dirk et al. |
| 2017/0231680 A1 | 8/2017 | Mahrenholz et al. |

FOREIGN PATENT DOCUMENTS

| | | |
|---|---|---|
| CN | 104871650 A | 8/2015 |
| DE | 10 2009 060 627 A1 | 6/2011 |
| DE | 10 2011 105 713 A1 | 12/2012 |
| DE | 10 2013 019 057 A1 | 5/2015 |
| DE | 10 2014 220 488 A1 | 4/2016 |
| EP | 2 883 426 A1 | 6/2015 |
| KR | 101407672 B1 | 6/2014 |
| RU | 2196394 C1 | 1/2003 |
| UA | 11022 C2 | 12/1996 |
| WO | 2002/094455 A1 | 11/2002 |
| WO | 2013/040542 A1 | 3/2013 |
| WO | 2015/070832 A1 | 5/2015 |

ELECTRODE ARRAY FOR A DIELECTRICALLY IMPEDED PLASMA TREATMENT

The invention relates to an electrode arrangement for a dielectric barrier discharge plasma treatment of a surface of an electrically conductive body used as a counter-electrode, with a flexible planar electrode and with a dielectric which is composed of a planar flexible material and which, with a layer preventing a direct current flow, shields the electrode from the surface to be treated, wherein the dielectric, by way of a structure with projections, can rest on the surface to be treated, and wherein air spaces for the formation of the plasma are formed between the projections.

DE 10 2009 060 627 B4 discloses such an electrode. Its configuration permits the formation of a planar flexible electrode arrangement which is adaptable even to irregularly curved surfaces, such that the electrode arrangement can be placed onto this surface in order to carry out a plasma treatment. To ensure that a plasma can develop, the dielectric is formed with a structure having projections with which the electrode arrangement can bear on the surface, and yet a plasma can still form in the air spaces between the projections. In said document, and in the context of this application, "air spaces" are understood as empty spaces which are usually filled with air, but which for certain uses can also be filled with a suitable gas in order to form special plasmas. The structure of the dielectric provided with the projections can be formed in one piece with the layer preventing the direct current flow from the electrode, or it can be produced as a separate component that can be connected to the layer mechanically, by form-fit engagement and/or by cohesive bonding. The planar flexible electrode is preferably completely embedded in the dielectric, wherein the dielectric can be composed of two layers between which the electrode, having a smaller two-dimensional extent, is inserted, after which the two layers of the dielectric are connected to each other. This can be done by cohesive bonding, in which the material of the dielectric is melted in the region of the partition surfaces, but also by use of a suitable insulating adhesive. In another embodiment, the planar electrode, which can be formed from a wire lattice, is encapsulated with the material of the dielectric in order to form the electrode arrangement by injection molding or in a molding process.

The known electrode arrangement has proven successful and is in particular also suitable for treatment of the surface of the skin of a human or animal body. The plasma treatment can improve the uptake of therapeutic or cosmetic active substances, such that the plasma treatment intensifies the desired therapeutic or cosmetic action. The plasma treatment moreover ensures effective disinfection, since it destroys micro-organisms and in particular has a bactericidal and fungicidal action on the skin.

For the treatment of the skin with medical or cosmetic active substances, it is obvious for these to be applied to the skin in combination with the electrode arrangement.

The problem addressed by the present invention is to maintain the known and proven electrode arrangement, with the advantages that it can afford, and yet improve it in terms of its production and its use in the cosmetics or medical sector.

To solve this problem, an electrode arrangement of the type mentioned at the outset is characterized, according to the invention, in that the structure is a lattice structure of mutually adjoining walls which delimit numerous chambers forming the air spaces, and in that the chambers are closed off at the bottom by the layer of the dielectric preventing the direct current flow and have a side which is open to the surface to be treated and of which the contact face for bearing on the surface to be treated consists of end edges of the walls of the lattice structure.

By virtue of the fact that the structure of the electrode arrangement defining the air spaces is designed as a lattice structure, it is possible to maintain the distance from the continuous layer of the dielectric, preventing the direct or galvanic current flow from the electrode, to the surface to be treated using a very flexible and light structure which is preferably composed of a non-absorbing material, i.e. which does not take up liquids. Suitable materials here are flexible silicones, in particular silicones sold under the trade name Silpuran® by Wacker Chemie. In this way, the electrode arrangement according to the invention is also suitable for the treatment of surfaces in which liquids are present or develop at the surface, as may be the case, for example, in a skin wound. The electrode arrangement according to the invention is thus also suitable as a wound dressing, since the material does not connect to the wound or to wound secretions, under which circumstances the removal of the electrode arrangement would result in a healed layer being torn open.

In a preferred embodiment of the invention, sets of walls, preferably two sets of walls, with walls at an angle to one another, form chambers as air spaces which are delimited by intersecting wall pairs. The lattice structure according to the invention is preferably formed by two sets of mutually parallel walls, wherein the walls of the two sets intersect. Rectangular chambers, but also diamond-shaped chambers, can in this way be obtained as air spaces, which are delimited by respectively two walls of the two sets. The material of the lattice structure can in principle be of any desired kind, for example also with greater or lesser electrical conductivity. However, a lattice structure is preferred which is made of a dielectric material, which can also be identical or similar to the material of the dielectric.

The formation of the chambers by two sets of mutually parallel walls has the advantage that chambers which are always of the same size are formed and are delimited by walls with a uniform wall thickness. The same effect can also be achieved if the lattice structure is a honeycombed structure composed of hexagonal honeycombs.

In a preferred embodiment, the two sets of walls are perpendicular to one another, resulting in the formation of rectangular chambers, preferably square chambers.

According to the invention, however, the lattice structure can also have chambers with a round, oval or polygonal cross section. The mutually adjacent walls of these chambers then form spandrels which can likewise serve as air spaces, such that the lattice structure has chambers of several sizes, in particular chambers of two sizes. However, it is also possible to fill the spandrels with the wall material in order to increase the stability of the lattice structure. In this case, the chambers are delimited by walls which have the same basic wall thickness but which are thicker in the spandrel region.

The walls preferably have an identical height, such that chambers are formed which are closed laterally and which form a closed-off air space when the electrode arrangement is placed onto the surface to be treated. Tests have shown that a suitable plasma can also be formed in closed-off chambers of this kind. This is the case even when the chambers are partially filled with a treatment material. The material can be introduced into the chambers in ointment and paste form, but also as an absorbable porous solid, in which case moreover a suitable plasma can be generated if the chambers are not completely filled.

The lattice structure according to the invention is particularly advantageous when the material thickness of the walls makes up less than 20%, preferably less than 10%, of the greatest width of a chamber. In this way, a very large volume is available for the plasma formation, wherein the lattice structure nonetheless ensures reliable spacing.

The material thickness of the walls is preferably between 0.1 and 1.0 mm, in particular between 0.4 and 0.6 mm. A desired stability of the spacing maintained by the lattice structure is also achieved with very flexible material if the height of the walls above the layer of the dielectric preventing the direct current flow is between 0.1 and 5 mm, preferably between 0.5 and 3 mm in particular between 1 and 2 mm.

The lattice structure can be formed in one piece with the layer of the dielectric preventing the current circuit. This configuration can be produced by a molding process. However, the lattice structure according to the invention also permits rapid build-up in the manner of a prototype in 3D printing.

The lattice structure according to the invention can also be produced as a separate part in the same manner, i.e. by a molding process or by 3D printing, in order then to be joined to the layer of the dielectric preventing the direct or galvanic current flow. A rigid connection between the lattice structure and the layer of the dielectric can then be produced in a customary manner, i.e. mechanically in a housing structure, by form-fit engagement and/or cohesive bonding, the latter by gluing or welding. The separate production of the lattice structure can have the advantage, particularly in the treatment of wounds, of permitting easy exchange of that part of the electrode arrangement coming into contact with the wound, wherein the separate part can be used as a removable disposable part or can also be easily sterilized on account of the small volume.

Particularly as an electrode arrangement suitable for wound treatment, an embodiment is preferred in which the planar electrode has through-openings distributed across its surface, and the dielectric shielding the electrode extends on both sides of the planar electrode and is provided with through-openings designed for draining fluid from the surface to be treated, said through-openings being in alignment with the through-openings of the electrode and having smaller dimensions than the through-openings of the electrode, such that the dielectric also completely covers the electrode in the region of the through-openings. Wound secretions can be drained off via these through-openings without the danger of flashover from the electrode to the skin via the wound secretions. The through-openings can also be used to guide a gas stream, if appropriate also as an air stream, onto the surface to be treated. However, it is expedient for the through-openings to be in alignment with chambers of the lattice structure in the region of the continuous layer.

The lattice structure according to the invention may be suitable for direct contact with a wound. However, it is also possible to apply a thin layer of a wound dressing material to the lattice structure so as to provide a high-quality wound dressing. The wound dressing material can also be located inside the lattice structure if it is open-pored and thus permits the formation of the plasma inside the lattice structure.

The invention is explained in more detail below on the basis of illustrative embodiments shown in the drawing, in which.

Figure 1:
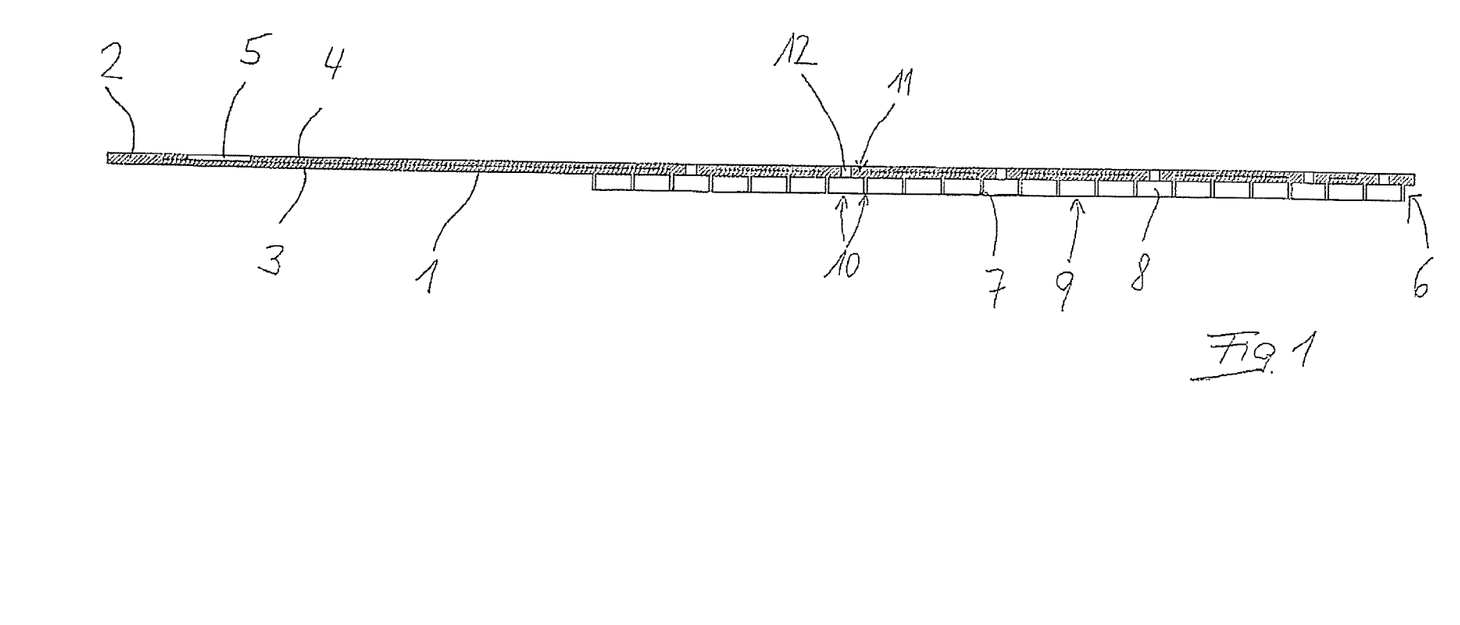
FIG. 1 shows a vertical section through a first illustrative embodiment of an electrode arrangement according to the invention.

The vertical section through an electrode arrangement according to a first embodiment shows a metallic, planar and flexible electrode 1 which is completely surrounded by a dielectric 2. In particular, the dielectric forms a lower layer 3 directed toward a surface to be treated, and an upper layer 4 directed away from the surface to be treated. The dielectric 2 has greater dimensions all round than the electrode 1, as a result of which the dielectric 2 completely covers the electrode 1. In particular, the lower layer 3 constitutes a layer 3 preventing the direct (galvanic) current flow between the electrode 1 and the surface (not shown) that is to be treated.

It will be seen from FIG. 1 that the upper layer 4 has, at an edge region of the electrode 1, a recess 5 via which a high voltage can be supplied to the electrode 1.

The lower layer 3 of the dielectric is adjoined integrally by a structure 6 in the form of a lattice structure which is formed by walls 7, 8 extending parallel to one another, wherein the walls 7, on the one hand, and the walls 8, on the other hand, respectively extend parallel to one another, and the walls 7 and 8 are perpendicular to one another. Formed between two pairs of walls 7 and 8 in each case is a rectangular chamber 9, preferably a square chamber 9, which is closed off at the bottom by the lower layer 3 preventing the direct current flow from the electrode 1. The chambers 9 are open on the other side. When the walls 7, 8, which are preferably of the same height, bear on the surface to be treated, their end edges 10 thus form the lattice-like contact face bearing on the surface to be treated.

It will also be seen from FIG. 1 that the electrode 1 has through-openings 11, in which a smaller through-opening 12 of the dielectric 2 is centrally located. The through-opening 11 of the electrode 1 is thus filled almost completely, i.e. except for the smaller through-opening 12, such that the electrode 1 is completely shielded by the dielectric 2 even in the region of the through-opening 12.

The through-openings 11, 12 are preferably aligned with a respective chamber 9 and permit removal of a fluid, in particular of a liquid, from the surface to be treated by way of the associated chamber 9.

The electrode arrangement configured in this way is suitable in particular for the treatment of a skin surface on which there is a wound, wherein a wound secretion can be removed via the through-openings 12 onto the distal surface of the electrode arrangement.

Figure 2:
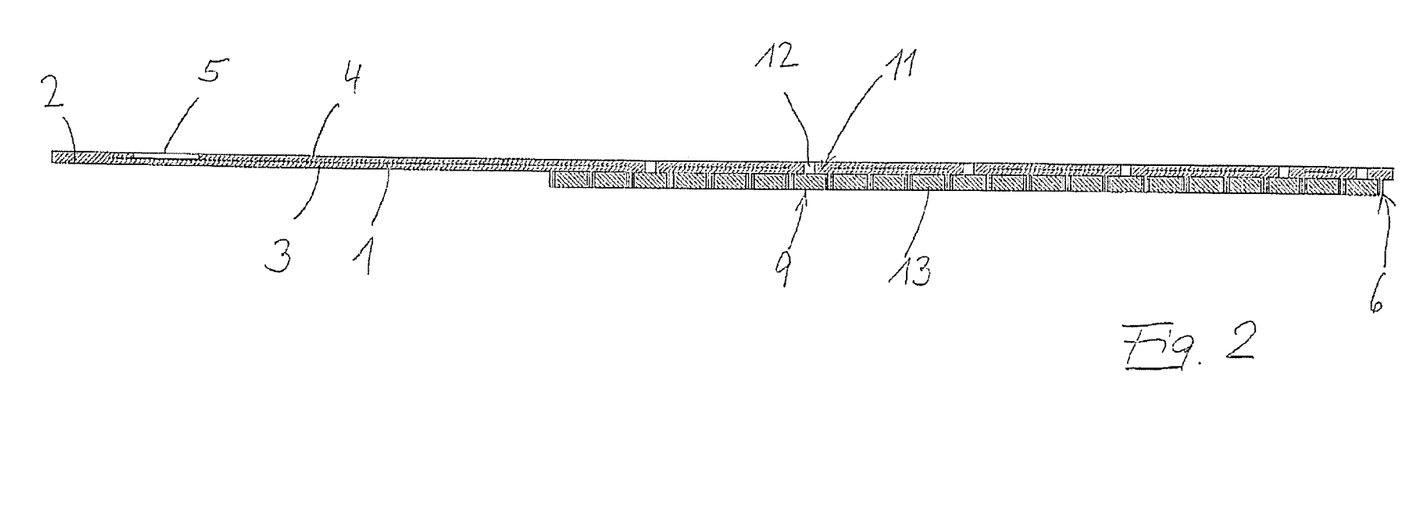
FIG. 2 shows a vertical section through a modification of the electrode arrangement according to the first embodiment.

FIG. 2, which shows a modification of the embodiment of the electrode arrangement in FIG. 1, simply indicates that the chambers 9 can be filled with a material 13, i.e. with a healing substance or skincare substance, for example collagen, or with a liquid-absorbing material, which can be like cotton wool and therefore ensures that there is still a sufficient air space for the formation of the plasma in the chambers 9. A non-porous or non-fibrous material, for example collagen, should fill the chambers 9 only partially, in order to ensure that a sufficient air space remains for the formation of the plasma.

By forming the dielectric 2 with the lattice structure 6 from a hydrophobic material, for example a suitable and skin-compatible silicone, it is possible to have the electrode arrangement bear directly on the skin surface or a wound. In this case, the end edges 10 of the walls 7, 8 bear directly on the skin surface or the wound. By virtue of the hydrophobic material, adherence of the lattice structure 6 to wound secretions is avoided, such that the electrode arrangement can be removed from the wound without tearing the wound open again.

However, it is also possible for a wound dressing material, for example in the form of a layer of gauze, to be applied to the end edges 10 of the walls 7, 8 of the lattice structure 6 in order thereby to ensure a sterile wound dressing.

Figure 3:
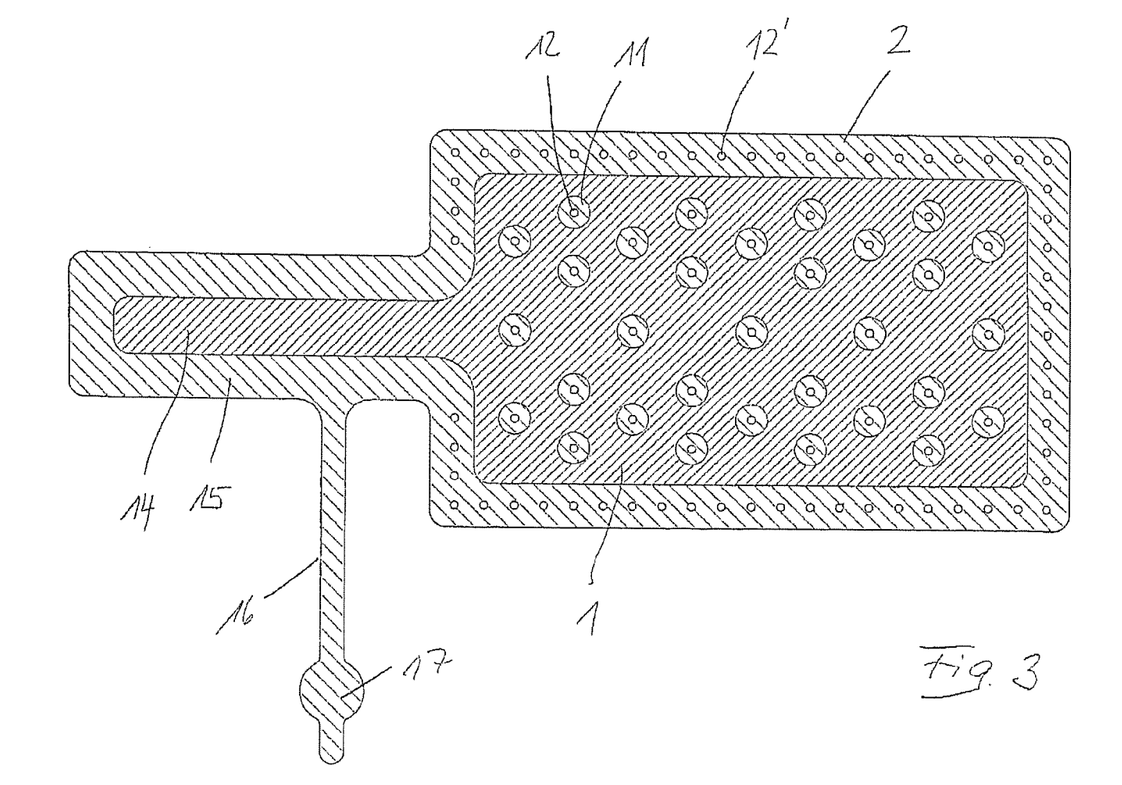
FIG. 3 shows a horizontal section at the level of the planar electrode of the electrode arrangement of the first embodiment.

FIG. 3 shows a horizontal section through the electrode arrangement according to FIG. 1 and reveals a configuration in which the electrode 1 forms an attachment tab 14, at which the contact through the recess 5 can be effected. In the region of the attachment tab 14 too, the electrode 1 is completely surrounded, except for the recess 5, by the dielectric 2, such that the dielectric also forms a tab structure 15. A flexible strip 16 with a cylindrical closure part 17 is formed integrally on the tab structure 15. The size of the cylindrical closure part 17 corresponds to the size of the recess 5 and serves to close the recess 5 when the electrode arrangement is not contacted.

It will be seen from FIG. 3 that the dielectric surrounds the substantially rectangular electrode 1 like a frame and extends beyond the electrode 1 on all sides. In the illustrative embodiment shown, further through-openings 12' are arranged in the strip-shaped region of the dielectric 2 extending beyond the electrode 1, which through-openings 12' likewise serve for the removal of gaseous or liquid substances from the surface to be treated, in particular for the removal of wound secretions from a wound.

It will be seen that the region of the electrode arrangement in which the attachment tab 14 of the electrode 1 and the tab structure 15 of the dielectric 2 are located is not intended to bear on the surface to be treated, and therefore there is also no lattice structure 6 in this region according to FIGS. 1 and 2.

Figure 4:
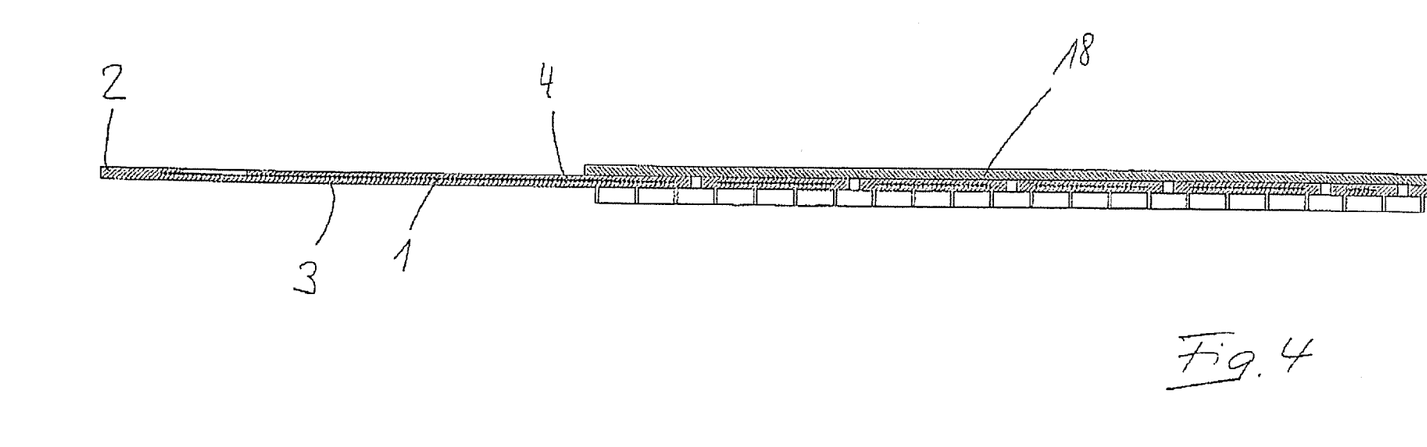
FIG. 4 shows a vertical section through an electrode arrangement according to a second illustrative embodiment.

FIG. 4 shows a vertical section, corresponding to FIG. 1, through a second embodiment of an electrode arrangement according to the invention. This embodiment is identical to the embodiment shown in FIG. 1 and simply has a sheet 18 of a material that absorbs wound secretions applied to the upper layer 4 of the dielectric above the lattice structure 6. This sheet 18 can be connected to the dielectric 2 by adhesive bonding or the like, but it can also be part of a secondary dressing with which the electrode arrangement is fixed to the surface to be treated.

The structure of the electrode arrangement according to the second embodiment is illustrated with reference to the exploded view in FIG. 5. The sheet 18 of the material that absorbs wound secretions is located on the side directed away from the surface to be treated. If this sheet 18 is omitted, the first embodiment of the electrode arrangement shown in FIG. 1 is obtained.

Located below the sheet 18 is the upper layer 4 of the dielectric 2 which, with an inner contour 19, receives the planar electrode 1. On the other side of the electrode 1, the lower layer 3 of the dielectric 2 is formed, with the lattice structure 6 of intersecting walls 7, 8 applied thereto.

Figure 5:
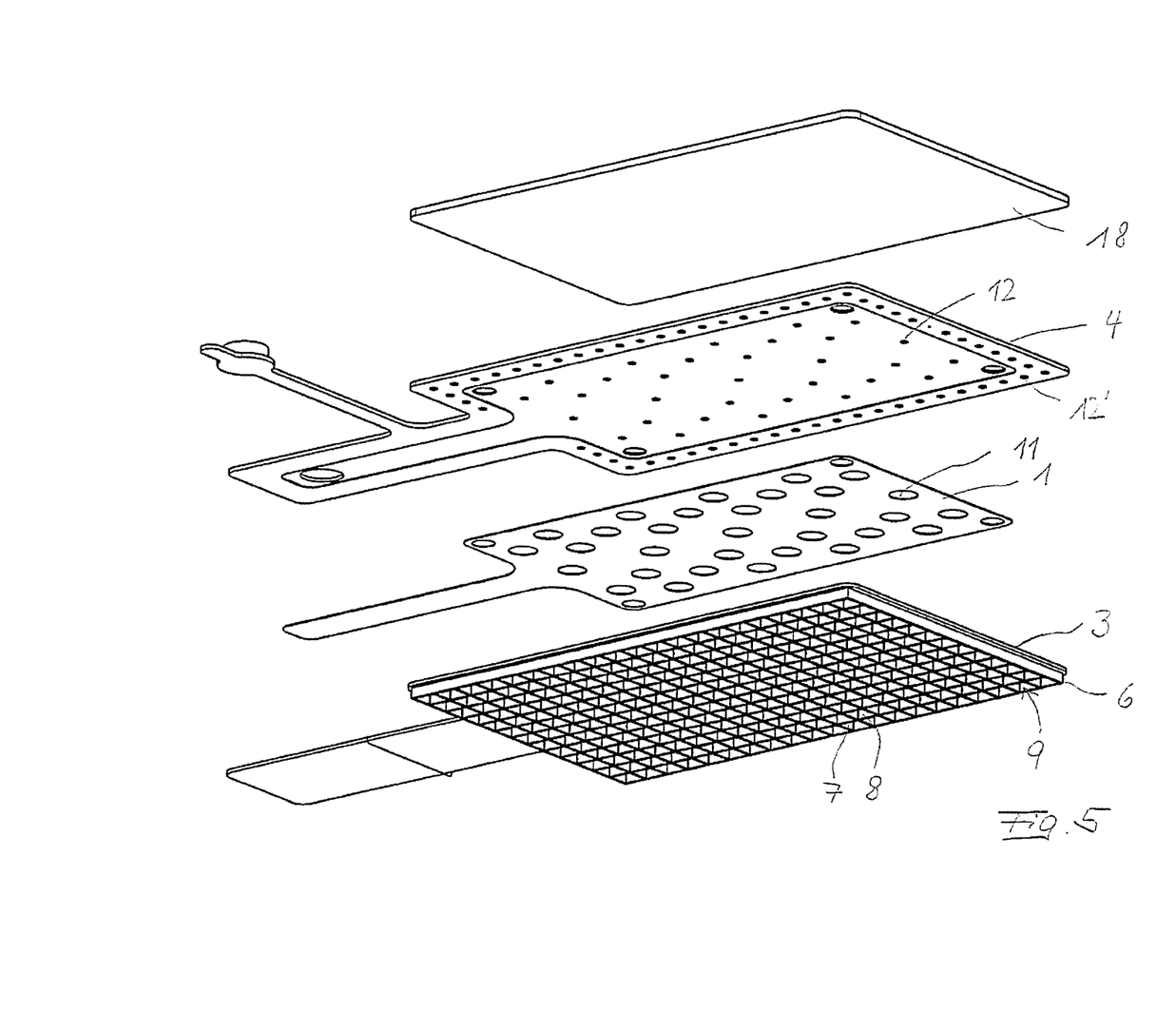
FIG. 5 shows a schematic exploded view of the electrode arrangement according to the second embodiment.

The exploded view in FIG. 5 serves merely as an illustration and does not entirely reflect the reality, since the dielectric 2 with the layers 3, 4 is are generally produced in a single method step by encapsulation of the electrode 1, in particular so as to ensure, within the through-openings 11 of the electrode 1, a continuous and complete insulation by the dielectric 2 except for the small through-openings 12. In principle, however, it is also conceivable to produce the dielectric 2 from two layers 3, 4, for example if through-openings 11, 12 are to be omitted, for example if removal of wound secretions does not appear necessary. Furthermore, it is of course also possible for the two layers 3, 4 to be connected to each other in a materially cohesive manner by hot plate welding, specifically in the frame-shaped enclosure region of the electrode 1, but also via the through-openings 11, maintaining the through-openings 12 of the dielectric 2.

Although the lattice structure 6 in the illustrative embodiments shown is depicted in one piece with the dielectric 2, it may be advantageous to produce the lattice structure 6 separately and fix it to the lower layer 3 of the dielectric 2. The lattice structure can be produced by molding with the aid of a corresponding die or also by 3D printing. By fixing the separately produced lattice structure 6 to the lower layer 3 in such a way that the former is easily exchangeable, it is possible, if so desired for reasons of sterility, to exchange the lattice structure 6 while retaining the rest of the electrode arrangement.

In order to supply a high voltage, preferably used as alternating voltage, that is required for the plasma generation, a jaw-like connection terminal is used to contact the electrode arrangement, which connection terminal safely and completely insulates the surface of the electrode 1 exposed in the recess 5, so as to rule out accidentally touching the electrode 1 supplied with high voltage. A suitable contacting arrangement is described and depicted in WO 2012/175066 A1, to which reference can therefore be made, and a renewed description can therefore be dispensed with.

FIGS. 6 to 10 show further embodiments of an electrode arrangement according to the invention which differ from one another in terms of the shape of the structure 6.

Figure 6:
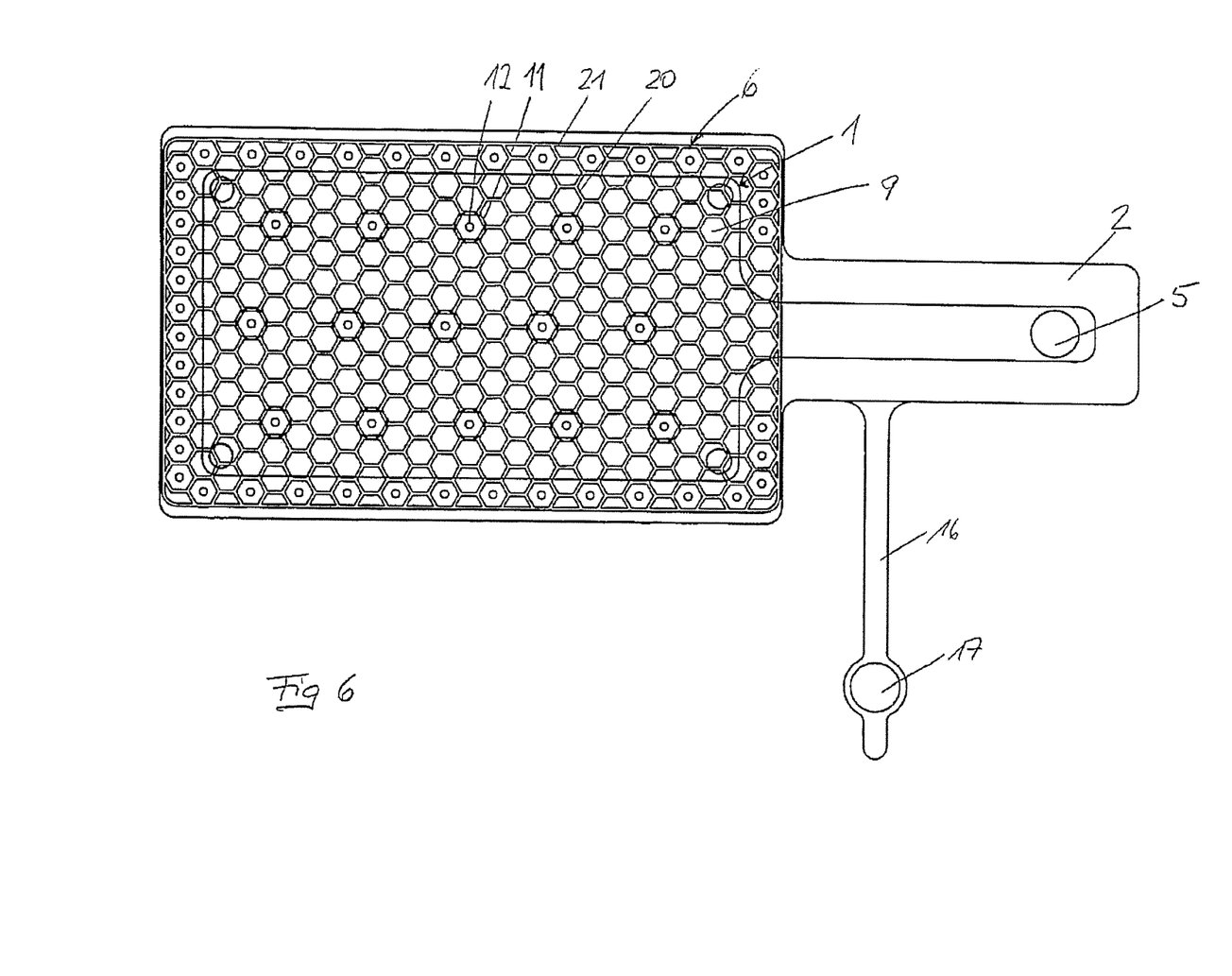
FIG. 6 shows a schematic plan view of the structure of an electrode arrangement according to a third embodiment.

According to the third embodiment, shown in FIG. 6, the chambers 9 of the structure 6 are honeycombed, that is to say are equilateral hexagons. In this way, the chambers 9 adjoin one another without gaps and are divided from each other by walls 20 of a constant wall thickness. The structure 6 is enclosed by a peripheral closure wall 21. In this embodiment too, which is otherwise the same as the first and second embodiments, through-openings 12 can extend through the dielectric 2 and are aligned with larger through-openings 11 in the planar electrode 1.

Figure 7:
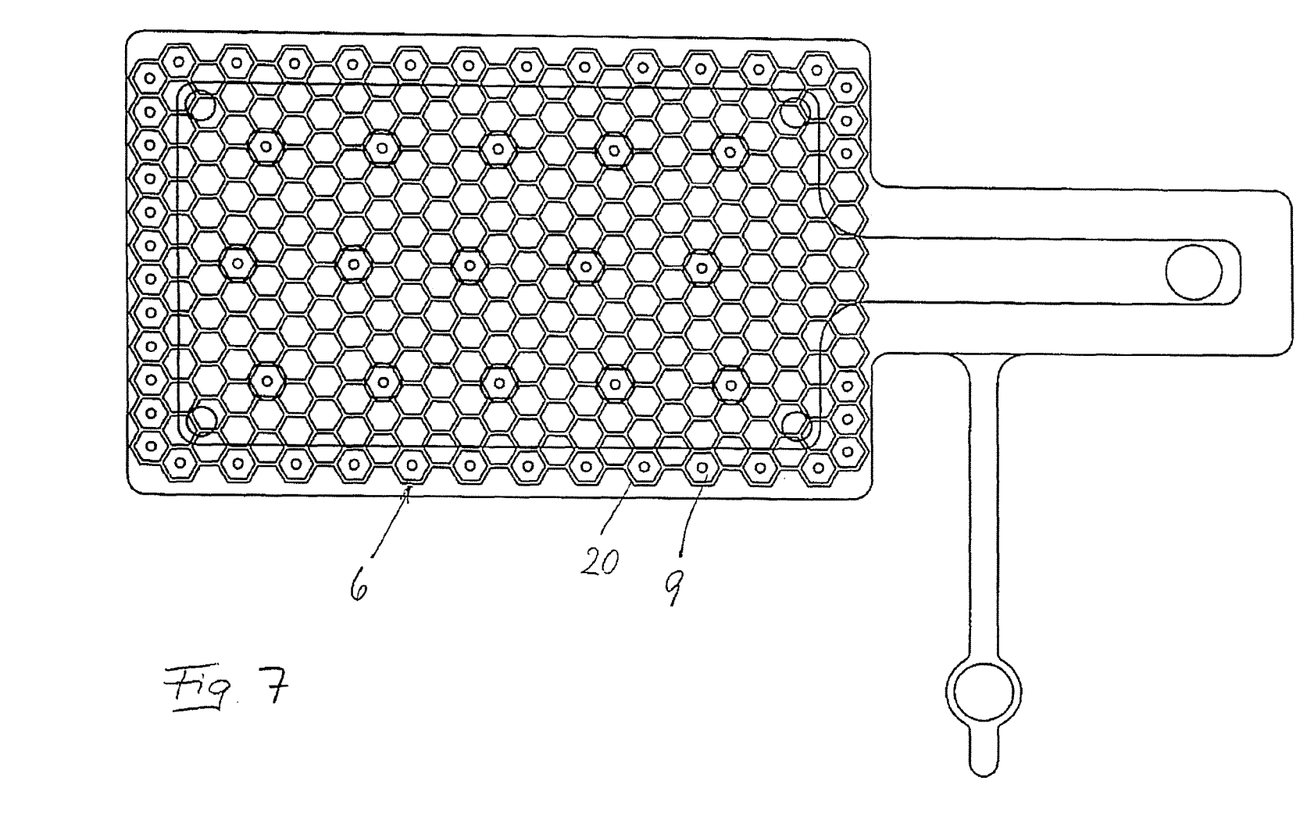
FIG. 7 shows a schematic plan view of the structure of an electrode arrangement according to a fourth embodiment.

The fourth embodiment of an electrode arrangement, shown in FIG. 7, corresponds to the configuration of the third embodiment according to FIG. 6 but is formed without a peripheral closure wall 21, such that the structure 6 is delimited by the meandering walls 20 of the chambers 9 at the edge of the structure 6. Here too, the structure 6 extends in both two-dimensional extents beyond the respective extent of the electrode 1, such that the structure 6 protrudes on all sides beyond the surface of the electrode 1.

Figure 8:
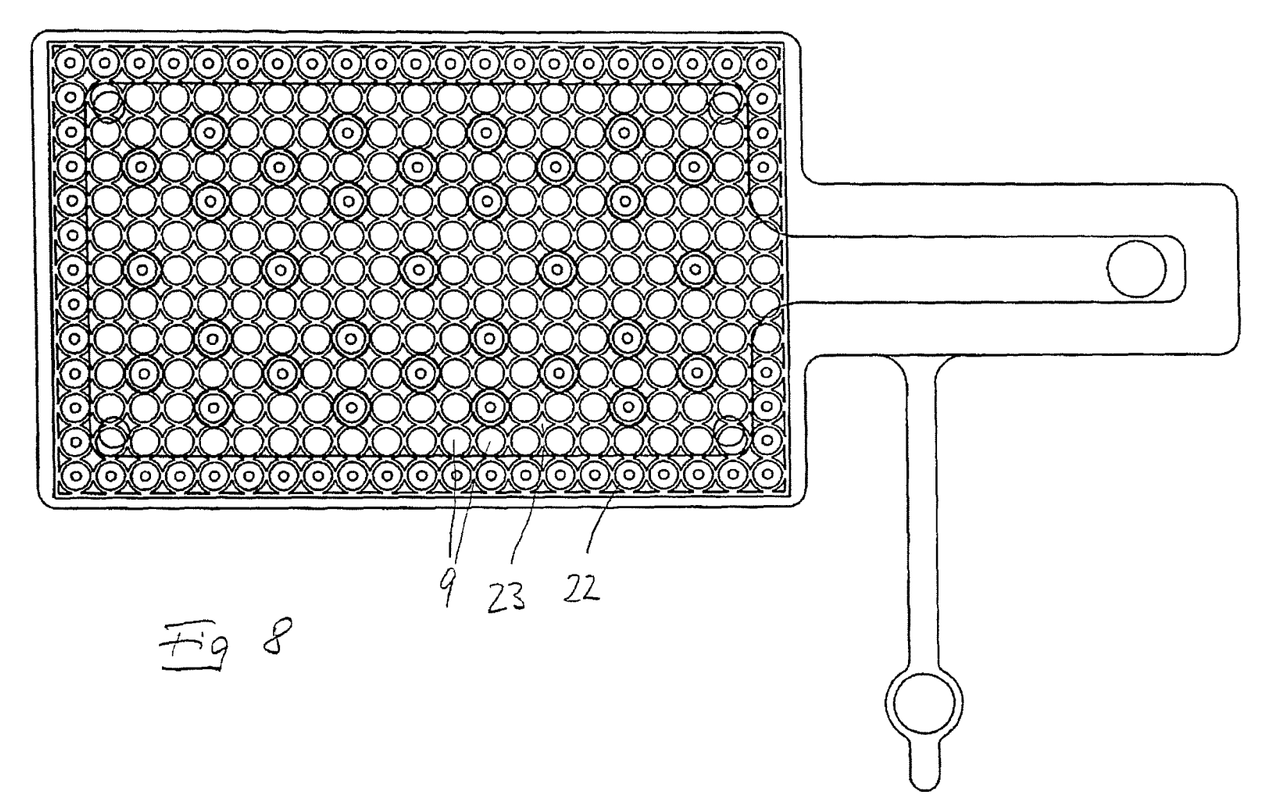
FIG. 8 shows a schematic plan view of the structure of an electrode arrangement according to a fifth embodiment.

In the fifth embodiment, shown in FIG. 8, the chambers 9 are circular and are delimited by corresponding hollow-cylindrical walls 22. Since the walls 22 are formed with a constant wall thickness, spandrel chambers 23 are obtained between the chambers 9, in which spandrel chambers 23 a plasma can likewise form. The rest of the configuration of the electrode arrangement corresponds to the preceding embodiments.

Figure 9:
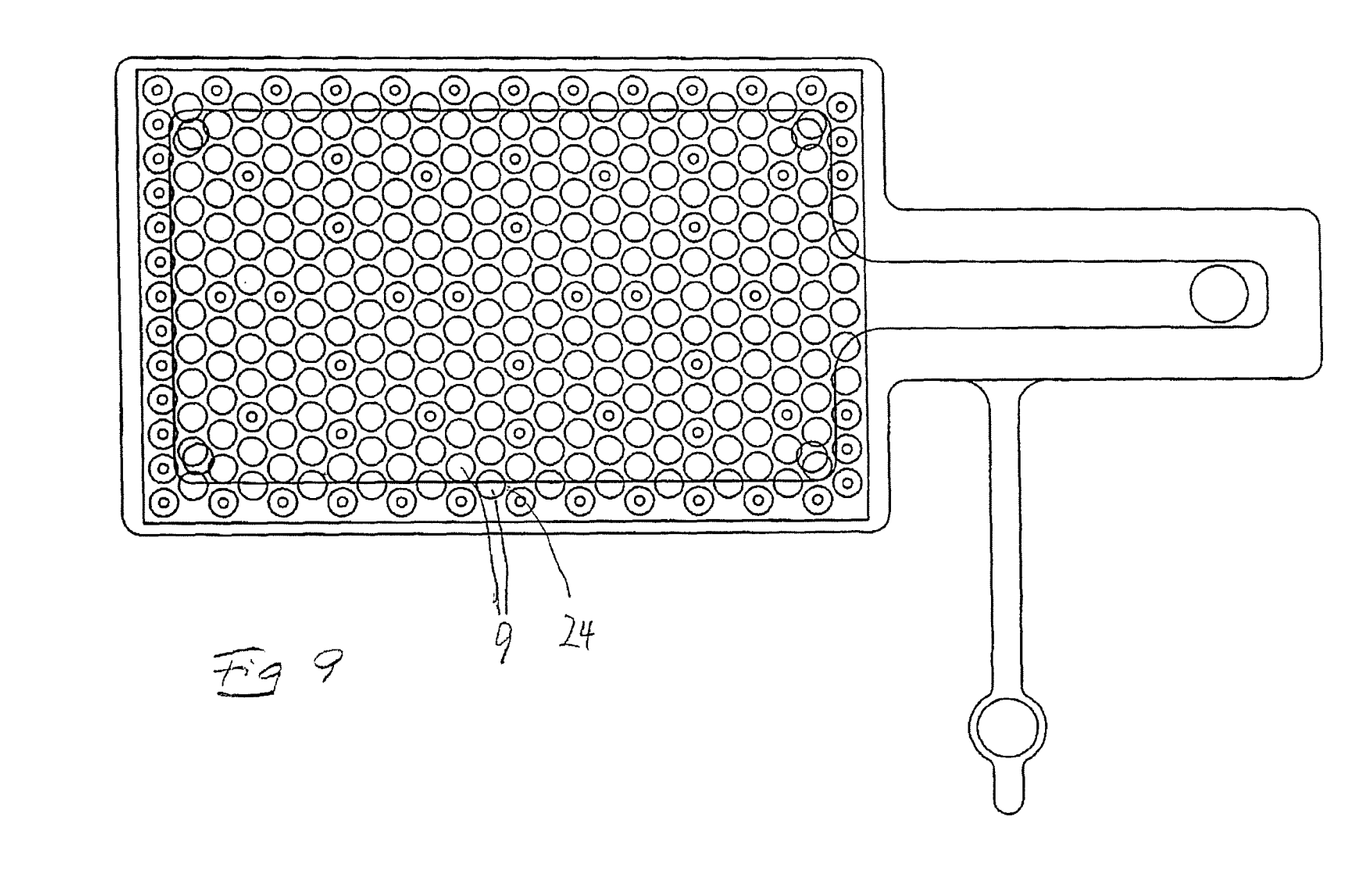
FIG. 9 shows a schematic plan view of the structure of an electrode arrangement according to a sixth embodiment.

In the sixth embodiment, shown in FIG. 9, the chambers 9 are likewise circular but are delimited by walls 24 which completely fill the space between the chambers 9 and accordingly have varying wall thicknesses. In this embodiment, the walls 24 are formed from more material than in the embodiment according to FIG. 8. The added consumption of material is limited by the fact that, in the embodiment according to FIG. 9, the chambers 9 of one row or column are offset in relation to the chambers 9 of the adjacent row or column, in each case by half a chamber width, whereas the chambers in the embodiment according to FIG. 8 form horizontal rows and vertical columns. The greater consumption of material for the embodiment according to FIG. 9 has to be set against simplified manufacture.

Figure 10:
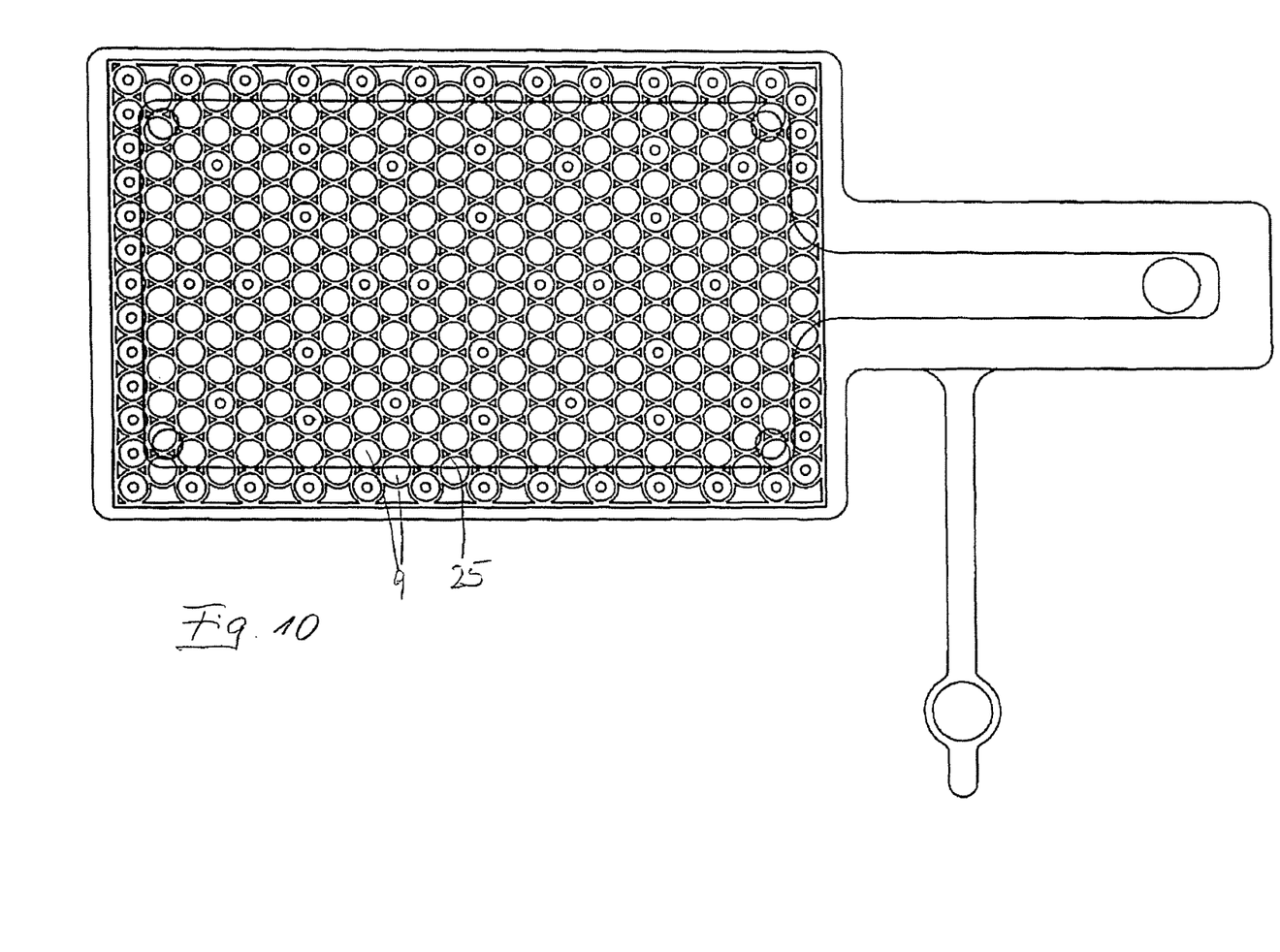
FIG. 10 shows a schematic plan view of the structure of an electrode arrangement according to a seventh embodiment.

In the seventh embodiment, according to FIG. 10, the circular chambers 9 are offset as in the sixth embodiment according to FIG. 9, wherein small spandrel chambers 25 are obtained which can be filled by a solid material of triangular shape or by a corresponding triangular hollow cylinder. The configuration of the electrode arrangement in this embodiment corresponds in other respects to that of the preceding embodiments.

It will be readily appreciated that other structures 6 can be formed with chambers 9 closed on all sides, wherein the chambers 9 can also be configured in different sizes, as is already the case of the chambers 9 and 23 shown in FIG. 8.

The invention claimed is:

1. An electrode arrangement for a dielectric barrier discharge plasma treatment of a surface of an electrically conductive body used as a counter-electrode, comprising:
    a flexible planar high voltage (hv) electrode;
    a dielectric which is composed of a planar flexible material and which, with a layer preventing a direct current flow from the flexible planar hv electrode to the electrically conductive body, shields the flexible planar hv electrode from the surface to be treated,
    wherein the dielectric, by way of a structure with projections, can rest on the surface to be treated,
    wherein air spaces for the formation of the plasma are formed between the projections,
    wherein the structure is formed as a lattice which has chambers forming the air spaces, and the chambers are closed off by the layer of the dielectric preventing the direct current flow and have a side which is open to the surface to be treated,
    wherein the chambers are delimited by mutually adjoining walls, wherein each wall has a material thickness of between 0.1 and 1.0 mm and a height of 0.5 to 3 mm,
    wherein the material thickness of each wall of the numerous walls makes up less than 20% of a greatest width of a chamber of the chambers,
    wherein a contact face for bearing on the surface to be treated consists of end edges of the at least some of the mutually adjoining walls of the lattice formed by the structure, and
    wherein the electrically conductive body is a dedicated counter-electrode that capacitively couples with the flexible planar hv electrode to produce the plasma.

2. The electrode arrangement as claimed in claim 1, wherein the lattice is composed of sets of numerous walls of the mutually adjoining walls wherein the sets of numerous walls are at an angle to one another, of which one chamber of the chambers is in each case delimited by two intersecting wall pairs.

3. The electrode arrangement as claimed in claim 2, wherein the numerous walls in the sets of numerous walls extend parallel to one another.

4. The electrode arrangement as claimed in claim 3, wherein two sets of walls of the sets of numerous walls exist whose walls are perpendicular to one another.

5. The electrode arrangement as claimed in claim 4, wherein the walls in cross section delimit square chambers.

6. The electrode arrangement as claimed in claim 1, wherein the chambers are formed with a round, oval or polygonal cross section.

7. The electrode arrangement as claimed in claim 1 wherein the material thickness of each wall of the numerous walls makes up less than 10% of a greatest width of a chamber of the chambers.

8. The electrode arrangement as claimed in claim 1 wherein the lattice is formed in one piece with the layer of the dielectric preventing the direct current flow.

9. The electrode arrangement as claimed in claim 1 wherein the lattice is a separate part that is joined to the layer of the dielectric preventing the direct current flow.

10. The electrode arrangement as claimed in claim 1 wherein the planar electrode has through-holes distributed across its surface, and wherein the dielectric extends on both sides of the planar electrode and has through-holes for draining fluid from the surface to be treated, wherein the through-holes of the dielectric are in alignment with the through-holes of the electrode and wherein the through-holes of the dielectric have smaller dimensions than the through-holes of the electrode such that the dielectric completely covers the electrode in the region of the through-holes of the dielectric.

11. The electrode arrangement as claimed in claim 10, wherein the through-holes of the dielectric are in alignment with the chambers of the lattice.

12. The electrode arrangement as claimed in claim 1 wherein the structure is composed of a dielectric material.

13. The electrode arrangement as claimed in claim 1, wherein the chambers are formed with a honeycombed cross section.

* * * * *